United States Patent [19]

Latham et al.

[11] Patent Number: 5,081,232

[45] Date of Patent: * Jan. 14, 1992

[54] COMPLEXES OF TC99M RADIOPHARMACEUTICALS

[75] Inventors: Ian A. Latham, Hove, England; John R. Thornback, Brussels, Belgium; Joanne L. Newman, Wolverhampton, England

[73] Assignee: Amersham International plc, Little Chalfont, England

[*] Notice: The portion of the term of this patent subsequent to Apr. 10, 2007 has been disclaimed.

[21] Appl. No.: 194,285

[22] Filed: May 16, 1988

[30] Foreign Application Priority Data

May 15, 1987 [GB] United Kingdom ............... 8711496

[51] Int. Cl.$^5$ ..................... C07F 13/00; A61K 36/14
[52] U.S. Cl. ........................................ 534/14; 424/1.1
[58] Field of Search ................ 534/14; 424/1.1

[56] References Cited

U.S. PATENT DOCUMENTS

| | | | |
|---|---|---|---|
| 4,374,821 | 2/1983 | Glavan et al. | 534/14 X |
| 4,387,087 | 6/1983 | Deutsch et al. | 534/14 X |
| 4,451,450 | 5/1984 | Subramanyam | 424/1.1 |
| 4,481,184 | 11/1984 | Kronauge et al. | 424/1.1 |
| 4,489,054 | 12/1984 | Deutsch et al. | 424/1.1 |
| 4,526,776 | 7/1985 | Subramanyam et al. | 534/14 X |
| 4,707,544 | 11/1987 | Jones et al. | 534/14 |

FOREIGN PATENT DOCUMENTS

85/03063 7/1985 PCT Int'l Appl. .

OTHER PUBLICATIONS

Radonovich and Hoard, J. Phys. Chem., vol. 88, No. 26, pp. 6711–6716, 1984.
Heitzmann et al., "Journal of Labelled Compounds and Radiopharmaceuticals" vol. XVII (No. 4), 535–543 (1981).
Eakins et al., "J. Chem. Soc.", 6012–6016 (1963).
Armstrong et al., "Inorg. Chem." 15(8), 1904–1909 (1976).

Primary Examiner—Brooks H. Hunt
Assistant Examiner—Ngoclan Mai
Attorney, Agent, or Firm—Wenderoth, Lind & Ponack

[57] ABSTRACT

Complexes useful as radiopharmaceuticals contain the $^{99m}$Tc-NO moiety and up to four organic ligands which confer biological target-seeking properties on the complex. Preferred are mono-cationic complexes, particularly having the formula $$[^{99m}Tc(NO)L_2X]^+$$

where X is halide or pseudohalide and L is a bidentate ligand for Technetium, which have interesting properties for use as heart visualizing agents. Examples of ligands include di-(dialkyl and diphenyl)phosphinoethanes and o-phenylenebisdimethylarsine. The complexes may be made by reacting generator eluate pertechnetate with a hydroxylamine salt and with the ligands, preferably in a single step by providing a reaction mixture containing the three reagents optionally in the presence of a reducing agent.

11 Claims, 2 Drawing Sheets

COMPLEXES OF TC99M RADIOPHARMACEUTICALS

FIELD OF INVENTION

This invention relates to radiopharmaceuticals including the $^{99m}$Tc-NO moiety, and to methods for their preparation involving the use of hydroxylamine salts.

BACKGROUND OF THE INVENTION AND PRIOR ART

Radiopharmaceuticals may be used as diagnostic or therapeutic agents by virtue of the physical properties of their constituent radionuclides. Thus, their utility is not based on any pharmacologic action. Most clinically used drugs of this class are diagnostic agents incorporating a gamma-emitting nuclide which, because of physical or metabolic properties of its coordinated ligands, localises in a specific organ after intravenous injection. The resultant images can reflect organ structure or function. These images are obtained by means of a gamma camera that detects the distribution of ionising radiation emitted by the radioactive molecules. The principal isotope currently used in clinical diagnostic nuclear medicine is metastable technetium-99m (t$_{\frac{1}{2}}$ 6 hrs).

The preparation of $^{99m}$Tc radiopharmaceuticals generally requires addition of generator-produced Na$^{99m}$TcO$_4$ eluate to a ligand or ligands in the presence of a reducing agent. Many reducing agents have been used to this effect including tin metal, stannous ion, sodium borohydride, ferrous ascorbate, ferrous ion and formamidine sulphonic acid. These procedures often lead to Tc complexes containing Tc=O moiety, where the technetium is in the +4 or +5 oxidation state. The formation of such radiopharmaceutical complexes can often occur via substitution reactions on $[Tc^VOX_5]^{2-}$ or $[Tc^{IV}X_6]^{2-}$ molecules, which has been identified as a route of significant synthetic utility (Deutsch E, Libson K., Jurisson S., Lindoy L. F., Technetium Chemistry and Technetium Radiopharmaceuticals, Prog. Inorg. Chem (1982) 30 p 175). Only under harsh reaction conditions in the presence of powerful reducing agents and/or strong acids or bases are Tc$^I$ oxidation state complexes attained and stabilised. A limitation to the formation of novel radiopharmaceutical products is the tendency towards formation of Tc=O species, but in addition formation of Tc$^{4+}$ or Tc$^{5+}$ complexes also limits the number and/or type of ligands prone to bind to the metal.

PCT Application WO 85/03063 describes the synthesis of the TcN moiety as an intermediate in the preparation of radiopharmaceuticals by virtue of its ability to undergo various ligand substitution reactions. The TcN core is again primarily based on the +5 oxidation state of Tc.

The reaction of TcCl$_6^{2-}$ with hydroxylamine salts under a variety of conditions to form a variety of complexes containing Tc-NO moiety have been described (Eakins, JCS (1963) 6012; Radonovich and Hoard, J Phys Chem, 88 (26) (1984) 6713; Armstrong and Taube, Inorg Chem (1976) 15 (3), 1904). This literature is concerned with $^{99}$Tc and not with its metastable isotope $^{99m}$Tc. $^{99}$Tc has a half life of 2.1×10$^5$ years, decays by emitting beta particles, and is of no interest as a radiopharmaceutical.

M. W. Heitzmann et al (Journal of Labelled Compounds and Radiopharmaceuticals, Volume XVIII No. 4, (1981) 535-543) has described a method for reacting pertechnetate ion (TcO$_4^-$) with hydroxylamine hydrochloride in the presence or absence of a reducing agent, to yield paramagnetic $^{99}$Tc complexes.

BRIEF SUMMARY OF THE INVENTION

This invention is based on the idea that complexes containing the $^{99m}$Tc-NO moiety would have interesting radiopharmaceutical properties in vivo, and that such complexes can be made from pertechnetate by a variety of simple routes involving hydroxylamine salts.

DETAILED DESCRIPTION OF THE INVENTION

Reference is directed to the accompanying drawings in which.

Figure 2:
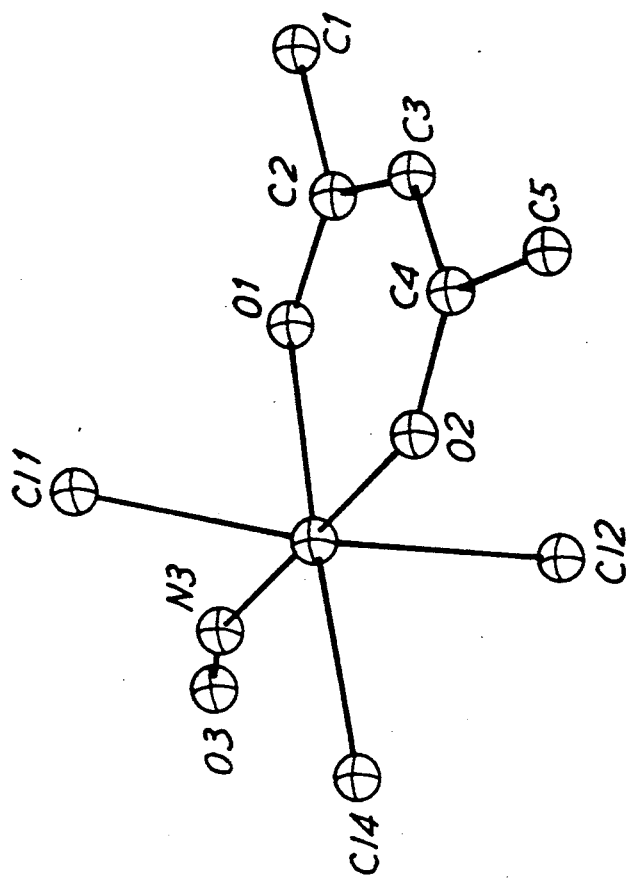
FIG. 2 shows the molecular structure of [Tc(NO)(acac)Cl$_3$]$^-$, (Example 14).

A first aspect of this invention relates to the reaction of $^{99m}$TcO$_4$M (Tc$^{99m}$ or pertechnetate, where M represents a cation such as alkali metal or ammonium) with hydroxylamine derivatives, in an aqueous medium. These reactions produce low oxidation state, anionic Tc compounds of uncertain composition, but which are known to contain the Tc-NO (Nitrosyl) moiety, (visible by infra red in $^{99}$Tc preparations). Commercially available hydroxylamine salts include NH$_2$OH.HCl, (NH$_2$OH)$_2$.H$_2$SO$_4$, and NH$_2$O-SO$_3$H, of which the first two examples are particularly preferred. Other salts are envisaged including the bromide, iodide and nitrate.

Alternatively it is possible to use a hydroxylamine derivative or salt thereof which can lead to the formation of Tc-NO moieties under appropriate conditions, e.g. via reaction to generate NH$_2$OH in situ. The hydroxylamine derivative may have the formula

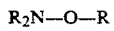

$$R_2N-O-R$$

where

R is H, OSO$_3$M or an activated alkyl or acyl leaving group such as -OCOR' or tosylate, R' is alkyl or aryl, and M is a cation such as alkali metal or ammonium.

Particularly when the hydroxylamine or derivative is used in the form of a sulphate or nitrate or other weakly co-ordinating salt, it may be helpful to include in the reaction mix a halide or pseudohalide such as SCN$^-$ or CN$^-$, so as to generate a ON-Tc-Halide or ON-Tc-SCN or ON-Tc-CN core.

The reduction of pertechnetate by hydroxylamine salts may be carried out by maintaining the reactants in an aqueous medium at ambient temperature or by heating at a temperature of at least 50° C., preferably by heating in a sealed vial at a temperature of 100° C. or more, for a time up to 60 minutes required to complete the reaction.

Formation of Tc-nitrosyl intermediates using NH$_2$OH.HCl has been found to proceed at ambient temperature to form a predominantly anionic complex, which on heating converts to an electrically netural intermediate species. These reactions have been conducted at $^{99}$Tc and $^{99m}$Tc levels where good chromatographic correlation is observed between the carrier free and carrier added preparations—Scheme 1.

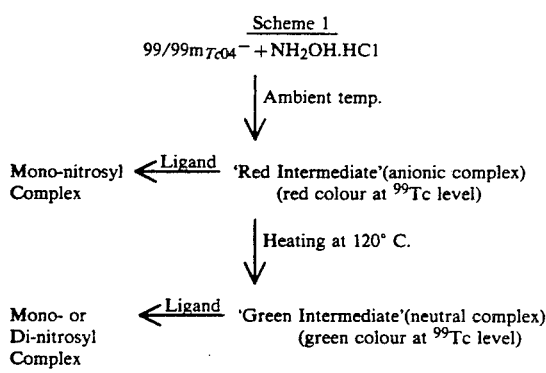

Scheme 1
$99/99mTcO_4^- + NH_2OH.HCl$

Ambient temp.

Mono-nitrosyl Complex ←Ligand— 'Red Intermediate'(anionic complex) (red colour at $^{99}$Tc level)

Heating at 120° C.

Mono- or Di-nitrosyl Complex ←Ligand— 'Green Intermediate'(neutral complex) (green colour at $^{99}$Tc level)

The addition of a known reducing agent for pertechnetate, such as tin metal, stannous ion, sodium borohydride, ferrous ascorbate, ferrous ion or formamidine sulphonic acid, (FSA) or bisulphite, may permit the reaction to be effected more quickly under milder conditions, e.g. at ambient temperature. It is possible to use for this purpose relatively weak reducing agents such as FSA and/or bisulphite in conjunction with rather high (e.g. at least 100 mg/ml) hydroxylamine levels; or stronger reducing agents such as stannous ion at lower hydroxylamine levels; the latter being preferred on account of the lower hydroxylamine concentration required.

The resulting $^{99m}$Tc-nitrosyl compounds are currently under investigation but are likely to be low oxidation state $Tc^I$ or $Tc^{II}$ or $Tc^{III}$ complexes stabilized by the capacity of the nitrosyl group to act as a good II acceptor ligand. The compounds have been shown to have considerable utility in the preparation of radiopharmaceuticals containing the Tc-NO moiety as described below.

In another aspect, the invention provides, as new compounds which are useful as radiopharmaceuticals, complexes containing the $^{99m}$Tc-NO moiety and a ligand which confers biological target seeking properties on the complex. These complexes are believed to contain Tc-99m generally in the 1+ or 2+ or 3+ state. They are often cationic. When the ligand is a bidentate ligand (L), they may have the formula $[^{99m}Tc(NO)_2L_2]^{n+}$ or $[^{99m}Tc(NO)L_2A]^{n+}$ where A is a monovalent anion such as halide and n is 1, 2 or 3. When the ligand is a monodentate ligand (L'), they may have the formula $[^{99m}Tc(NO)_2L'_4]^{n+}$ or $[^{99m}Tc(NO)L'_4A]^{n+}$. When the ligand is a tetradentate ligand (Q), they may have the formula $[^{99m}Tc(NO)_2Q]^{n+}$ or $[^{99m}Tc(NO)QA]^{n+}$. A wide range of ligands for these complexes are envisaged, including:

a) Phosphines and arsines of the general formula $R_2Y(CZ_2)_nYR_2$, where Y is P or As; R is H or aryl or substituted or unsubstituted alkyl, preferably C1–C4 alkyl or phenyl; n is 1, 2, 3 or 4; and $(CZ_2)$ is a substituted or unsubstituted methylene group. Related compounds are described in: U.S. Pat. Nos. 4,481,184, 4,387,087, 4,489,054, 4,374,821, 4,451,450, 4,526,776, GB 8624272 (Amersham International; methylene bridged diphosphine complexes), GB 8723438 (Amersham International; phosphines containing ether groups), and ligands of general type $R_mY—(CH_2)_n—X—(CH_2)_n—X—(CH_2)_n—YR_m$ where
Y is P or As,
X is NR, S, Se, O, P or As,
R is H or hydrocarbon such as C1–C6 alkyl or aryl,
m is 1 or 2, and
n is 1, 2, 3 or 4.

b) Methylene Diphosphonate (MDP)
c) Thiourea (TU)
d) Thiomalate (TMA)
e) Dimercaptosuccinic acid (DMSA)
f) Gluconate (GLUC)
g) Ethane-1-hydroxy-1,1-diphosphonate (EHDP)
h) Diethylene triamine pentaacetic acid (DTPA)
i) N-(2,6-[Dialkyl]phenyl carbamoylmethyl) iminodiacetate

| alkyl | = | Methyl (HIDA) |
|---|---|---|
| | | Ethyl (EHIDA) |
| | | $^i$Propyl (PIPIDA) | j) Dialkyl dithiocarbamate
k) Isonitriles of the general type C N≡R R=alkyl, alkoxy, ether
l) BAT Derivatives—of the general type illustrated below, and specifically:
  i) $R_1=R_7=H$, $R_{2,3,5,6}=Et$, $R_4=$N-methylspiropiperidinyl,
  ii) $R_1=R_7=H$, $R_{2,3,5,6}=Et$, $R_4=$N-ethylspiropiperidinyl,
  iii) $R_1=R_7=H$, $R_{2,3,5,6}=Et$, $R_4=$N-isopropylspiropiperidinyl,

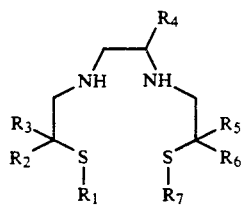

m) phenathroline,
n) pentane-2,4-dione,
o) bipyridyl,
p) Other ligands having propylene amine oxime backbone of the general structural types described in EPA 123504 and 194843:

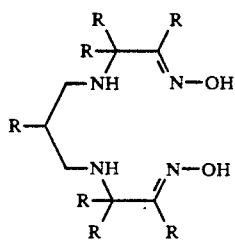

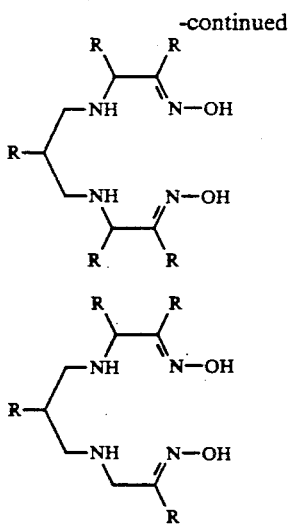

where the various groups R=various H and/or alkyl and/or aryl substituents.

These complexes can be prepared by various methods, which form additional aspects of this invention:

a) Reaction of the $^{99m}$Tc-NO compounds described above with a suitable ligand. Reaction conditions depend on the nature of the ligand, but typically involve holding the reactants at ambient or elevated temperature in an aqueous medium.

b) Reaction of suitable preformed $^{99m}$Tc radiopharmaceutical complexes with hydroxylamine salts. This can result in exchange of e.g. halogen, oxo (mono or bis oxo complexes), phosphine or isonitrile ligands for nitrosyl groups. Again, reaction conditions depend on the particular ligand involved, but generally involve holding the reactants at ambient or elevated temperature in an aqueous medium.

c) A one-step preparation, in which pertechnetate, e.g. from a technetium generator, is added to a mixture of a hydroxylamine salt and the chosen ligand. In this reaction, the hydroxylamine salt is acting as a reducing agent. As compared with stannous ion and other reducing agents, hydroxylamine salts have the advantage, as previously noted, of being able to reduce technetium to a low oxidation state provided that the ligand is capable of stabilizing technetium in that state. As before, reaction conditions depend on the nature of the ligand, but typically they involve holding the reactants at ambient or elevated temperature in an aqueous medium.

The desirability of using a substitution route for the preparation of $^{99m}$Tc radiopharmaceuticals has long been recognised. The problem with this approach is obtaining the $^{99m}$Tc intermediate at a carrier free level, and in a state or medium which is amenable to substitution reactions. The nitrosyl labelling techniques here described are simple methods for the preparation of a wide range of radiopharmaceuticals based on the Tc-NO moiety. In all cases studied to date, the presence of the nitrosyl group has been found to alter the biological behaviour of the $^{99m}$Tc complex. For example, the propylene amine oxime complexes described in EPA 123504 and 194843 are neutral and have the ability to pass through the blood brain barrier; whereas propylene amine oxime complexes of $^{99m}$Tc-NO according to this invention are positively charged and do not enter the brain.

The following Examples illustrate the invention. Examples 1 to 3 show the preparation and properties of the intermediate $^{99m}$Tc-NO species. Examples 4 to 12 show different methods for the preparation of various complexes, suitable for use as radiopharmaceuticals, containing the $^{99m}$Tc-NO moiety.

Example 13 shows preparation and characterization of the $[Tc^{II}(NO) Cl_4]^-$ anion. Examples 14 to 18 show preparation via the anion and properties of various other complexes. Example 19 reports X-ray diffraction studies of the complex $[Tc(NO)(dppe)_2Cl]^+Cl^-$.

In some Examples, results using $^{99}$Tc are reported as indication of the result obtainable with $^{99m}$Tc.

EXAMPLE 1

Preparation of Tc-NO sulphate Intermediate

Materials

| | |
|---|---|
| $(NH_2OH)_2.H_2SO_4$ | 500 mg |
| Water (AnalaR) | 1 ml |
| $^{99m}$TcO$_4$Na (generator eluate) | 0.5 ml (5 GBq/ml) |

Preparation

Saline, (0.1 ml) was added to 500 mg $(NH_2OH)_2.H_2SO_4$ in a $N_2$ purged sealed reaction vessel to which $^{99m}$TcO$_4$Na was added to give a final radioactive concentration of 1-25 GBq/ml in 2 ml. The resulting solution was heated at 120° C. for 15 minutes.

After cooling, the product was submitted to various analytical techniques, the results of which are summarised below, with animal biodistribution data.

Chromatography Data

The final 'intermediate' solution contains no colloid and no free pertechnetate, and indicates that the technetium-99m complex is present in solution in approximately 95% yield:

| | |
|---|---|
| Saline | rf = 0.9 |
| Methylethylketone | rf = 0.0 |
| Acetonitrile/Water 50:50 | rf = 0.7 (broad) |

Gel Electrophoresis Data

Agarose gel, run at pH 7.4 in 50 mM phosphate buffer, approx. 35 min, indicates that this species is a mixture of electrically natural (origin) and anionic species, observed via movement towards the cathode. rf= +0.62 to +1.6 (+ indicating movement towards cathode)

Infra red data on $^{99}$Tc analogue

The orange/red reaction $^{99}$Tc product formed in an identical fashion to the $^{99m}$Tc preparation contains (NO)=1830–1840 cm$^{-1}$ (broad).

HPLC data 2-solvent Gradient HPLC system
a) 20 mM Phosphate Buffer pH 7.4
b) Tetrahydrofuran (THF) (Initially 100% (a) going to 100% (b) within 17 minutes).
Flow rate=2 ml/min
Hamilton PRP column (15 cm×4.0 mm)
Ambient Temperature Result: This complex elutes in the void of this system <2 minutes.

Animal Biodistribution Data

Average values for studies involving 6 rats (3 at 2' and 3 at 60'). Table of Data—see over (Table 1).

TABLE 1
ANIMAL BIODISTRIBUTION DATA
Results for Tc-nitrosyl-sulphate intermediate in rats

| Time p.i. in vivo | 2 min Mean | Std. Dev. | 60 min Mean | Std. Dev. |
|---|---|---|---|---|
| % injected dose/organ | | | | |
| Heart | 0.42 | 0.06 | 0.18 | 0.03 |
| Blood | 23.16 | 3.28 | 8.00 | 0.69 |
| Muscle | 28.03 | 0.93 | 11.74 | 0.75 |
| Lung | 1.62 | 0.18 | 0.82 | 0.11 |
| Liver | 4.84 | 0.34 | 3.89 | 0.80 |
| Liver + GI | 11.65 | 1.19 | 9.65 | 1.97 |
| Kidney + Urine | 8.69 | 1.46 | 40.71 | 2.97 |
| Brain | 0.07 | 0.00 | 0.03 | 0.00 |
| Counts/Gram ratio | | | | |
| Heart/Blood | 0.30 | 0.06 | 0.34 | 0.04 |
| Heart/Muscle | 1.78 | 0.16 | 1.72 | 0.14 |
| Heart/Liver | 1.11 | 0.09 | 0.58 | 0.15 |
| Heart/Lung | | | | |

EXAMPLE 2(a)

Preparation of $^{99m}$Tc-NO 'Red' Chloro-intermediate

Materials

| | |
|---|---|
| NH$_2$OH.HCl | 500 mg |
| Saline | 1.0 ml |
| $^{99m}$TcO$_4^-$ generator elute | 1.0 ml (2.5 GBq/ml) |

Preparation

Saline was added to the 500 mg NH$_2$OH.HCl and $^{99m}$TcO$_4$ generator eluate. The reaction mixture was left at ambient temperature for 30 minutes.

The product was submitted to various analytical techniques, the results of which are summarised below.

Chromatography Data

The product solution contained no free pertechnetate or reduced technetium colloid.

| Saline | rf = 1.0 | (sharp) |
|---|---|---|
| Methylethylketone | rf = 0.27 | 2 discrete species |
| | 0.74 | 50:50 |
| Acetonitrile/Water 50:50 | rf = 0.82 | (sharp) |

Gel Electrophoresis Data

Agarose gel, shows predominantly one complex present rf = +1.3 [free TcO$_4^-$ runs at +1.99].

Infra-red Data $^{99}$Tc

The dark red solid isolated showed a band at (NO) = 1780 cm$^{-1}$ (broad).

HPLC Data

This complex elutes <2 minutes (void volume) of the HPLC system.

EXAMPLE 2(b)

Preparation of $^{99m}$Tc-NO Green Intermediate

Materials

| | |
|---|---|
| NH$_2$OH.HCl | 500 mg |
| Saline | 1 ml |
| $^{99m}$TcO$_4^-$ generator elute | 1.0 ml (2.5 GBq/ml) |

Method

The reaction mixture was sealed in a glass vial and heated to 120° for 30 minutes (this reaction also proceeds very slowly 2-3 hours at ambient temperature). The resulting mixture was left to cool and submitted to the usual analytical techniques.

Chromatography Data

The final solution of this 'intermediate' contains no colloid, and no free pertechnetate and indicates that the $^{99m}$Tc complex is present in approximately 95% yield.

| Saline | rf = 1.03 | (sharp) |
|---|---|---|
| Methylethylketone | rf = 0.03 | 2 discrete species |
| | 0.68 | |
| Acetonitrile/Water 50:50 | rf = 0.61 | (sharp) |

Gel Electrophoresis

| rf = 0.05 | Electrically neutral, complex remains at the origin |
|---|---|

HPLC Data

This complex elutes via <2 mins in this system. Animal Biodistribution of mixture of 'red' and 'green' Tc-NO intermediates: Table 2.

Infra-red Data $^{99}$Tc Complex

This pale green solid exhibited a band of (NO) = 1785cm$^{-1}$ (very similar to red intermediate).

TABLE 2
ANIMAL BIODISTRIBUTION DATA

| Time p.i. in vivo | 2 min Mean | Std. Dev. | 60 min Mean | Std. Dev. |
|---|---|---|---|---|
| % injected dose/organ | | | | |
| Heart | 0.45 | 0.05 | 0.32 | 0.04 |
| Blood | 22.18 | 1.95 | 12.87 | 1.16 |
| Muscle | 27.59 | 1.98 | 18.08 | 1.72 |
| Lung | 1.92 | 0.26 | 1.35 | 0.26 |
| Liver | 5.93 | 0.22 | 5.62 | 0.38 |
| Liver + GI | 13.28 | 0.78 | 13.36 | 1.97 |
| Kidney + Urine | 6.67 | 1.78 | 20.81 | 1.98 |
| Brain | 0.09 | 0.03 | 0.03 | 0.02 |
| Counts/Gram ratio | | | | |
| Heart/Blood | 0.33 | 0.02 | 0.39 | 0.03 |
| Heart/Muscle | 1.98 | 0.26 | 2.05 | 0.10 |
| Heart/Liver | 0.99 | 0.09 | 0.68 | 0.06 |
| Heart/Lung | | | | |

EXAMPLE 2 (c)

Correlation of $^{99m}$Tc rection products derived from 'red' or 'green' intermediates, have been attempted by generating the intermediate then reacting these with the same target seeking ligand, e.g. 1,10-phenanthroline. Results from this work suggest little difference between the products derived from red or green intermediate (as set out below) at the $^{99m}$Tc level after treatment under indentical conditions, Table 2(c).

TABLE 2 (c)

|  | Product from Phen + Red Intermediate | Product from Phen + Green Intermediate |
|---|---|---|
| Chromatography | | |
| Saline | rf = 0.0 | rf = 0.0 |
| MEK | rf = 0.0 | rf = 0.0 |
| ACN/W 50:50 | rf = +0.99 | rf = 0.75 (broad to 0.99 |
| Gel electrophoresis | | |
| Complex | rf +1.03 | rf +1.03 |
| HPLC retention time (min) | 2 peaks (broad) 15-17' | 2 peaks (broad) 15-17' |

EXAMPLE 3

Simplified Preparation of Tc-Nitrosyl Intermediates in the Presence of known Reducing Agents Materials

| NH$_2$OH.HCl | 400 mg | |
|---|---|---|
| TcO$_4$Na | 1 ml | (GBq/ml) | e.g. Forrmamidine Sulphonic Acid (FSA) 5 mg

Preparation

Sodium 99m-pertechnetate solution (generator eluate) (0.4 ml) was added to 400 mg NH$_2$OH.HCl in 0.6 ml H$_2$O. This solution was then added to a second vial containing 5 mg formamidine sulphonic acid, to give a final radioactive concentration of 1-25 GBq/ml. The resulting solution was left to stand at ambient temperature for 15 minutes. The product was then submitted to various analytical techniques, the results of which are summarised below. The experiment was repeated using sodium bisulphite (5 mg) or 50 μg or Sn$^{2+}$ e.g. SnCl$_2$, in place of FSA with essentially the same results.

Chromatography Data

The final intermediate solution contains no colloid and no free pertechnetate, and indicates that the 99m-technetium complex is present in solution in approximately 95% yield.

| Saline | rf = +0.97 |
|---|---|
| Methylethylketone | rf = +0.54 |
| Acetonitrile/water 50:50 | rf = +0.34 |

Gel Electrophoresis Data

Agarose gel—conditions as described earlier.
Result: This complex consists of predominantly electrically neutral species and some minor anionic components rf=0 to −1.0 (− indicating movement towards the anode).

HPLC Data

This species also elutes <2 mins. in the HPLC system described earlier.

EXAMPLE 4

Preparation of $^{99m}$Tc-Nitrosyl-Phosphine Radiopharmaceuticals in aqueous solution.

$^{99m}$Tc-nitrosyl 'intermediate' from Examples 1, 2 or 3

| bis (diethylphosphino)ethane (DEPE) | 25 ul |
|---|---|

Preparation

The aqueous solution of $^{99m}$Tc nitrosyl intermediate described in Example(s) 1, 2 or 3 was mixed with 25 ul of bis(diethylphosphino)ethane, (or similar ligands) the resulting solution being heated at 120° C. for 30 minutes. The product was thus formed in 100% aqueous solution, and after appropriate pH adjustment (if necessary) and filtering through a sterile 0.22 u membrane filter, the radiopharmaceutical was ready to use.

EXAMPLE 5

Preparation of $^{99m}$Tc-Nitrosyl-Phosphine Radiopharmaceuticals in Aqueous/Ethanolic Solution (50:50%).

$^{99m}$Tc-nitrosyl 'intermediate' from Examples 1, 2 or 3

| bis(diphenylphosphino)ethane (DPPE) | 15 mg |
|---|---|
| Ethanol | 2 ml |

Preparation 2 ml of aqueous $^{99m}$Tc-nitrosyl intermediate were mixed with N$_2$ purged ethanolic solutions of bis(diphenylphosphino)ethane (2 ml). The resulting solutions were heated at 120° C. for 30 minutes.

The resulting products were pH adjusted (if necessary) and filtered through a sterile 0.22μ membrane filter, leaving the radiopharmaceutical products ready for use.

EXAMPLE 6

Direct one-step Preparation of $^{99m}$Tc-Nitrosyl-Phosphine Radiopharmaceuticals in Aqueous Solution

| $^{99m}$TcO$_4$−Na$^+$ (generator eluate) | 0.5 ml (5GBq/ml) |
|---|---|
| bis(dimethylphosphino)ethane (DMPE) | 2.5 μl |
| NH$_2$OH.HCl | 278 mg |
| H$_2$O | 2 ml |

Preparation

Hydroxylamine hydrochloride was dissolved in 2 ml H$_2$O to which $^{99m}$TcO$_4$−Na$^+$ (generator eluate) and DMPE (25 μl) were added. The resulting solution was heated at 120° C. for 30 minutes. After filtering through a sterile 0.22μ membrane filter the radiopharmaceutical preparation was ready for use.

In another experiment, bis(dimethylphosphino) propane (DMPP) was used in place of DMPE.

EXAMPLE 7

Transformation of Tc=O Core to Tc-NO+ Core by Reaction of $^{99m}$Tc=O Radiopharmaceuticals with Hydroxylamine Salts

| | |
|---|---|
| Ceretec TM kit (Amersham International) (RR,SS)-4,8-diaza-3,6,6,9-tetramethyl undecane-2,10-dione-bisoxime (HMPAO) | 0.5 mg |
| Stannous Chloride dihydrate | 7.6 μg |
| Sodium Chloride | 4.5 mg |
| $^{99m}$TcO$_4$—Na$^+$ (generator eluate) | 0.5 ml (5GBq/ml) |
| Saline (0.9% NaCl) | 4.5 ml |
| NH$_2$OH.HCl | 178 mg |
| H$_2$O | 2 ml |

Ceretec (d, l) HMPAO was reconstituted according to the procedure outlined in the pack leaflet, to produce radiochemically pure lipophilic [$^{99m}$Tc=O(HMPAO)] complex. Hydroxylamine hydrochloride was dissolved in water, and the two solutions were mixed. The resulting solution was left at ambient temperature for 30 minutes, after filtration through a sterile 0.22μ membrane filter the radiopharmaceutical products are ready for use.

EXAMPLE 8

Transformation of Tc(O)$_2^+$ core to Tc-NO core by reaction of $^{99m}$Tc-Dioxo complex with hydroxylamine salts

[$^{99m}$Tc(O)$_2$(depe)$_2$]$^+$ was prepared in good yield by the literature route (6), or by heating $^{99m}$TcO$_4$Na$^+$ with excess DEPE in saline at 120° for 30 mins. After appropriate checks of radiochemical purity, the [$^{99m}$Tc(O)$_2$(depe)$_2$]$^+$ solution was added to 50 mg of NH$_2$OH.HCl. Conversion to a cationic $^{99m}$Tc-(NO)-(depe) complex occurs slowly at room temperature, but is quickened by further heating e.g. (120°30'). The resulting radiopharmaceutical is indistinguishable from a cationic $^{99m}$Tc-(NO)-(depe) complex made via the Tc-NO intermediate route outlined earlier, i.e. by comparison of ITLC, HPLC and gel electrophoresis data.

Examples of biodistribution data for these and like processes are summarised in Tables 3 to 7. Summaries and correlation of the chromatographic properties of $^{99m}$Tc are given in subsequent Tables 8 and 9.

TABLE 3

ANIMAL BIODISTRIBUTION DATA
Cationic $^{99m}$Tc—(NO)-(Depe) Complex in sulphate form: Example 4

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 0.83 | 0.03 | 0.78 | 0.22 |
| Blood | 6.56 | 0.48 | 0.44 | 0.17 |
| Muscle | 20.6 | 5.1 | 17.0 | 2.1 |
| Lung | 1.66 | 0.17 | 0.84 | 0.29 |
| Liver | 24.8 | 3.0 | 4.34 | 1.11 |
| Liver + GI | 40.3 | 1.4 | 54.3 | 4.3 |
| Kidney + Urine | 11.1 | 1.7 | 15.3 | 1.6 |
| Brain | — | — | — | — |
| | Counts/Gram ratio | | | |
| Heart/Blood | 1.86 | 0.13 | 27.6 | 5.6 |
| Heart/Muscle | 4.50 | 0.71 | 4.97 | 0.16 |
| Heart/Liver | 0.38 | 0.08 | 2.06 | 0.24 |
| Heart/Lung | 0.8 | 0.1 | 1.4 | 0.3 |

TABLE 4

ANIMAL BIODISTRIBUTION DATA
Cationic $^{99m}$Tc—(NO)-(Dmpe) Complex in chloride form: Example 4

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 0.46 | 0.02 | 0.30 | 0.11 |
| Blood | 9.96 | 0.28 | 1.02 | 0.50 |
| Muscle | 27.00 | 1.28 | 14.10 | 3.70 |
| Lung | 1.09 | 0.00 | 0.33 | 0.17 |
| Liver | 15.03 | 0.59 | 3.14 | 0.93 |
| Liver + GI | 26.33 | 1.46 | 34.70 | 2.52 |
| Kidney + Urine | 10.18 | 0.75 | 42.60 | 4.71 |
| Brain | 0.04 | 0.02 | 0.01 | 0.00 |
| | Counts/Gram ratio | | | |
| Heart/Blood | 0.68 | 0.04 | 4.48 | 0.45 |
| Heart/Muscle | 1.85 | 0.15 | 2.34 | 0.56 |
| Heart/Liver | 0.38 | 0.00 | 1.13 | 0.18 |
| Heart/Lung | 0.71 | 0.00 | 1.53 | 0.33 |

TABLE 5

ANIMAL BIODISTRIBUTION DATA
Cationic $^{99m}$Tc—(NO)-(Dmpe) Complex: Example 6

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 0.86 | 0.12 | 0.62 | 0.06 |
| Blood | 31.6 | 0.7 | 5.79 | 0.87 |
| Muscle | 13.0 | 1.4 | 14.8 | 2.0 |
| Lung | 7.38 | 1.98 | 5.16 | 1.80 |
| Liver | 39.0 | 3.4 | 43.6 | 2.0 |
| Liver + GI | 42.7 | 3.3 | 58.4 | 8.6 |
| Kidney + Urine | 2.54 | 0.33 | 2.39 | 0.09 |
| Brain | — | — | — | — |
| | Counts/Gram ratio | | | |
| Heart/Blood | 0.38 | 0.04 | 1.68 | 0.18 |
| Heart/Muscle | 6.82 | 0.19 | 4.69 | 0.33 |
| Heart/Liver | 0.27 | 0.05 | 0.16 | 0.02 |
| Heart/Lung | 0.2 | 0.0 | 0.2 | 0.1 |

TABLE 6

ANIMAL BIODISTRIBUTION DATA
Cationic $^{99m}$Tc—(NO)-(Dmpp) Complex: Example 6

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 1.00 | 0.20 | 0.76 | 0.08 |
| Blood | 2.50 | 0.16 | 0.26 | 0.04 |
| Muscle | 33.36 | 0.90 | 32.15 | 0.53 |
| Lung | 0.97 | 0.17 | 0.50 | 0.03 |
| Liver | 16.43 | 0.63 | 2.98 | 0.33 |
| Liver + GI | 32.34 | 5.16 | 45.96 | 4.63 |
| Kidney + Urine | 10.6 | 2.21 | 13.14 | 6.21 |
| Brain | 0.04 | 0.00 | 0.02 | 0.00 |
| | Counts/Gram ratio | | | |
| Heart/Blood | 5.96 | 0.84 | 40.91 | 4.73 |
| Heart/Muscle | 3.32 | 0.58 | 2.44 | 0.09 |
| Heart/Liver | 0.76 | 0.21 | 3.15 | 0.48 |
| Heart/Lung | — | — | — | — |

TABLE 7

ANIMAL BIODISTRIBUTION DATA
Exchange of Tc=O for Tc—NO+ by reaction of radiopharmaceuticals with hydroxylamine salts e.g. Ceretec ™ Example 7.

| | 2 min | | 60 min | |
|---|---|---|---|---|
| | Mean | Std. Dev. | Mean | Std. Dev. |
| | % injected dose/organ | | | |
| Heart | 0.26 | 0.03 | 0.05 | 0.01 |
| Blood | 12.3 | 1.2 | 1.29 | 0.11 |
| Muscle | 20.1 | 1.0 | 2.9 | 0.3 |
| Lung | 0.98 | 0.22 | 0.15 | 0.02 |
| Liver | 28.9 | 0.4 | 18.8 | 2.8 |
| Liver + GI | 36.5 | 0.5 | 59.3 | 1.8 |
| Kidney + Urine | 9.33 | 1.07 | 32.3 | 2.59 |
| Brain | 0.4 | 0.1 | 0.0 | 0.0 |
| | Counts/Gram ratio | | | |
| Heart/Blood | 0.36 | 0.01 | 0.50 | 0.03 |
| Heart/Muscle | 1.62 | 0.11 | 1.69 | 0.10 |
| Heart/Liver | 0.23 | 0.01 | 0.03 | 0.00 |
| Heart/Lung | 0.03 | 0.0 | 0.4 | 0.1 |

EXAMPLE 9

$^{99m}$Tc(NO)Cl(DEPE)$_2$CHLORIDE FORM, 2-Step PREPARATION

Materials

| | |
|---|---|
| NH$_2$OH.HCl | 50 mg |
| $^{99m}$TcO$_4^-$ generator elute | 1 ml (2.5 GBq/ml) |
| DEPE | 251 μl |
| Saline | 4 ml |
| (DEPE in bis(diethylphosphino)ethane) | |

Method $^{99m}$TcO$_4^-$ generator eluate solution was added to a sealed N$_2$ filled vial containing NH$_2$OH.HCl and heated at 120° C. for 30 minutes. Saline was then added along with DEPE, the resulting mixture re-heated for a further 30' at 120° C. The product was cooled and submitted to various analytical techniques and animal biodistribution.

TABLE 8

SUMMARY OF CHROMATOGRAPHIC DATE FOR $^{99m}$Tc RADIOPHARMACETUCIALS: COMPARISON WITH $^{99}$Tc COMPLEXES

| Tc | Cationic Tc—(NO) Complex with EXAMPLE | ITLC DATA:rf Saline | MEK | MeCN/H$_2$O | GEL ELECTROPHORESIS GM = (−10xrf) | HPLC Retention time (mins) |
|---|---|---|---|---|---|---|
| 99m | Depe, sulphate form | +0.02 | +0.17 (45%) +0.79 (48%) | +0.78 | +6.7 (70%) +0.6 (20%) | 5.0', 6.2', 6.7', 7.5' and 8.2' mixture |
| 99m | Dmpe, chloride form | +0.06 | +0.03 (44%) +0.46 (42%) +0.68 (6%) | +1.00 | +10.9 (100%) | 4 species 5.04', 5.76', 6.8' and 7.8' |
| 99m | Dppe, chloride form | +0.03 | +0.67 | +0.90 | 0.0 (100%) | 2 species 9.3' and 11.0' |
| 99m | Ceretec | +0.09 | +0.12 | +0.84 | +1.6 (85%) | 2 species 4.8' and 6.6' |
| 99 | Dmpe, chloride form | +0.01 | +0.91 (25%) streaky | +0.87 | | 2 species 5.88' and 6.45' |
| 99 | Dppe, chloride form | +0.02 | +0.89 (55%) streaky | +0.86 | | 1 peak 10.86' (broad) |

Chromatography

| | |
|---|---|
| Saline (ITLC) | rf = 0.0 |
| MEK | rf = 0.77 |

TABLE 9

SUMMARY OF PHYSICAL CHARACTERISTICS OF $^{99}$Tc-NITROSYL-PHOSPHINE COMPLEXES

| Complex | MICROANALYSIS RESULTS % Found | | % Calculated + | | $^{99}$Tc—HPLC Retention time (min) | Infra Red cm$^{-1}$ | ν (NO) |
|---|---|---|---|---|---|---|---|
| Dmpe, PF$_6$ Salt [Tc(NO)(DMPE)$_2$Cl]$^+$PF$_6^-$ | C<br>H<br>N<br>Cl | 23.3<br>5.4<br>2.5<br>6.8 | C<br>H<br>N<br>Cl | 23.6<br>5.2<br>2.2<br>5.8 | 2 species 5.88' (45%) 6.48' (55%) | 1708 (S) | |
| Dppe, chloride form [Tc(NO)(DPPE)$_2$Cl]$^+$Cl$^-$ H$_2$O | C<br>H<br>N<br>Cl<br>P | 61.1<br>5.0<br>1.1<br>6.3<br>10.5 | C<br>H<br>N<br>Cl<br>P | 61.5<br>4.9<br>1.3<br>7.0<br>12.4 | 1 complex 10.68 | 1705 (S) | |
| Dppe chloride form* [Tc($^{15}$NO)(DPPE)$_2$Cl]$^+$ Cl$^-$ H$_2$O | C<br>H<br>N<br>Cl<br>P | 61.5<br>4.8<br>0.87<br>5.3<br>11.0 | C<br>H<br>N<br>Cl<br>P | 61.5<br>4.9<br>1.3<br>7.0<br>12.4 | 1 complex 10.56 | 1675 (S) | |
| Dppe, sulphate form | C<br>H<br>N<br>S<br>Cl | 58.9<br>5.0<br>1.2<br>3.1<br><0.03 | C<br>H<br>N<br>S<br>Cl | 61.1<br>4.7<br>1.3<br>3.1<br>0.0 | 4 species 8.7' (5%) 9.7 (10%) 10.8' (70%) 12.1' (10%) | 1700 (S) 1755 (W) 1840 (W) | broad |

*Synthesised from 99% $^{15}$NH$_2$OH.HCl
+for [Tc(NO)B$_2$A] where B is the diphosphine and A is the anion
$^{15}$N underestimated by this method of analysis -continued

| acetonitrile/Water 50:50 | rf = 0.96 |

This indicated that the complex is formed >95% pure with no free $TcO_4^-$ or reduced Tc-colloid.

Gel Electrophoresis

The complex is cationic rf=−0.47.

HPLC

The complex elutes at 8.0 minutes in this system.

Animal Biodistribution Result

See Table 10.

TABLE 10

ANIMAL BIOSTRIBUTION DATA IN RATS
$[^{99m}Tc(NO(DEPE)_2Cl]^+$ CHLORIDE FORM

|  | Time p.i. in vivo | | | |
|---|---|---|---|---|
|  | 2 min | | 60 min | |
|  | Mean | Std. Dev. | Mean | Std. Dev. |
|  | % injected dose/organ | | | |
| Heart | 1.06 | 0.17 | 0.92 | 0.14 |
| Blood | 6.00 | 0.74 | 0.41 | 0.08 |
| Muscle | 22.9 | 4.6 | 19.1 | 4.1 |
| Lung | 2.98 | 0.24 | 1.57 | 0.14 |
| Liver | 23.63 | 3.5 | 7.54 | 0.82 |
| Liver + GI | 37.3 | 4.3 | 47.0 | 3.1 |
| Kidney + Urine | 13.8 | 1.0 | 19.3 | 0.5 |
|  | Counts/Gram ratio | | | |
| Heart/Blood | 3.03 | 0.39 | 38.1 | 1.3 |
| Heart/Muscle | 5.94 | 0.74 | 6.18 | 0.86 |
| Heart/Liver | 0.73 | 0.17 | 1.75 | 0.28 |
| Heart/Lung | 0.4 | 0.0 | 0.6 | 0.1 |

EXAMPLE 10

$[^{99m}Tc(NO)X(DIARS)_2]^+$ COMPLEX CHLORIDE FROM 1-STEP PREPARATION USING AN ARSENIC LIGAND, LOW HYDROXYLAMINE LEVELS AND STANNOUS REDUCING AGENT

Materials

| $NH_2OH.HCl$ | 25 mg |
| $SnF_2$ solution | 1 ml 8 μg/ml |
| Saline | 3.0 ml |
| $^{99m}TcO_4^-$ generator elute | 1 ml (s.5 GBq/ml) |
| DIARS | 10 μl |
| (DIARS in o-phenylene-bis-(dimethylarsine)) | |

Method

To a sealed $N_2$ filled vial containing $NH_2OH.HCl$, $SnF_2$ solution, saline, $^{99m}TcO_4^-$ generator eluate, and DIARS ligand were added. The resulting mixture was heated at 120° C. for 60 minutes, cooled and submitted to the usual analytical techniques. After filtering through a sterile 0.22μ membrane filter the radiopharmaceutical preparation was ready for use.

Chromatography

The final solution contained no free $TcO_4^-$ or reduced technetium colloid, and indicates that the $^{99m}$ technetium complex is present in solution in approximately 95% yield.

| Saline | rf = 0.0 |
| MEK | rf = 0.29 |
| Acetonitrile/Water 50:50 | rf = 0.83 |

Gel Electrophoresis

The complex is cationic moving with an rf=−0.55.

HPLC

This complex elutes at 7 minutes in this system.

Animal Biodistribution Results

See Table 11.

TABLE 11

ANIMAL BIODISTRIBUTION DATA IN RATS FOR
$[^{99m}Tc(NO) \times (DIARS)_2]^-$

|  | Time p.i. in vivo | | | |
|---|---|---|---|---|
|  | 2 min | | 60 min | |
|  | Mean | Std. Dev. | Mean | Std. Dev. |
|  | % injected dose/organ | | | |
| Heart | 0.90 | 0.09 | 0.69 | 0.04 |
| Blood | 5.37 | 0.33 | 0.54 | 0.06 |
| Muscle | 20.8 | 4.7 | 14.5 | 2.5 |
| Lung | 1.42 | 0.15 | 0.63 | 0.03 |
| Liver | 20.7 | 2.1 | 5.84 | 0.56 |
| Liver + GI | 36.4 | 3.0 | 43.4 | 1.2 |
| Kidney + Urine | 15.6 | 1.5 | 28.5 | 1.7 |
|  | Counts/Gram ratio | | | |
| Heart/Blood | 2.40 | 0.05 | 20.4 | 1.80 |
| Heart/Muscle | 4.72 | 0.81 | 5.64 | 0.71 |
| Heart/Liver | 0.56 | 0.10 | 1.69 | 0.25 |
| Heart/Lung | 1.0 | 0.2 | 2.0 | 0.2 |

EXAMPLE 11

$^{99m}[Tc(NO)Cl(PMPE)_2]^+$ COMPLEX 1-STEP PREPARATION LOW HYDROXYLAMINE AND STANNOUS ROUTE

PMPE=bis(n-propylmethylphosphino)-ethane

Materials

| $NH_2OH.HCl$ | 25 mg |
| $SnF_2$ solution | 1 ml 8 μg/ml |
| Saline | 3.3 ml |
| $TcO_4^-$ generator elute | 0.7 ml (RAC = 2.5 GBq/ml) |

Method

As described for DIARS complex.

Chromatography

The final solution contained no free $TcO^{4-}$ or reduced technetium colloid, and indicates that the radiopharmaceutical complex is present in solution in approximately 95% yield.

| Saline | rf = 0.0 |
| MEK | rf = 0.75 |
| Acetonitrile/Water 50:50 | rf = 1.0 |

Gel Electrophoresis

The complex is cationic moving with an rf=−0.70.

HPLC

This complex elutes at 7 minutes in this system.

Animal Biodistribution Results

See Table 12.

TABLE 12
ANIMAL BIODISTRIBUTION DATA IN RATS
[$^{99m}$Tc(NO) × (PMPE)$_2$]$^+$

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 0.92 | 0.05 | 0.77 | 0.03 |
| Blood | 3.27 | 0.17 | 0.42 | 0.03 |
| Muscle | 21.1 | 3.9 | 17.5 | 3.5 |
| Lung | 1.40 | 0.16 | 0.53 | 0.08 |
| Liver | 27.4 | 3.5 | 6.23 | 0.70 |
| Liver + GI | 44.7 | 4.3 | 53.6 | 2.0 |
| Kidney + Urine | 13.3 | 1.1 | 15.2 | 1.3 |
| | Counts/Gram ratio | | | |
| Heart/Blood | 4.15 | 0.63 | 27.8 | 0.3 |
| Heart/Muscle | 4.78 | 0.28 | 5.01 | 0.95 |
| Heart/Liver | 0.44 | 0.10 | 1.65 | 0.14 |
| Heart/Lung | 1.0 | 0.1 | 2.3 | 0.3 |

EXAMPLE 12

$^{99m}$Tc-NITROSYL-MDP NITROSYL CORE INCORPORATED INTO MEDRONATE II BONE AGENT COMPLEX (COMMERCIAL KIT)

Materials

| | |
|---|---|
| NH$_2$OH.HCl | 500 mg |
| Saline | 1.5 ml |
| $^{99m}$TcO$_4^-$ generator elute | 0.7 ml (2.5 GBq/ml) |
| Medronate II Bone Agent Kit | (Amersham International) |
| (The Medronate II kit is based on methylene diphosphonate). | |

Method

Saline and $^{99m}$TcO$_4^-$ eluate were added to a sealed vial containing NH$_2$OH.HCl, the mixture was left at ambient temperature for 15 minutes. The resulting solution was added to the Medronate II kit, and was analysed after standing for 10 minutes at room temperature.

Chromatography

The resulting solution contained no free TcO$_4^-$ or reduced technetium colloid, the radiopharmaceutical complex was present in solution in approximately 95% yield.

| Saline | rf = 0.8 (very broad) |
|---|---|
| MEK | rf = 0.0 (sharp) |
| ACN/H$_2$O 50:50 | rf = 0.70 (broad) |

Gel Electrophoresis

The complex is anionic as expected and moves with an rf = +2.0.

HPLC

This complex elutes in the void volume of this system.

Animal Biodistribution Results

See Table 13.

TABLE 13
ANIMAL BIODISTRIBUTION DATA IN RATS
[$^{99m}$Tc(NO) (MDP)] COMPLEX

| | Time p.i. in vivo | | | |
|---|---|---|---|---|
| | 2 min | | 60 min | |
| | Mean | Std. Dev. | Mean | Std. Dev. |
| | % injected dose/organ | | | |
| Bone | — | — | 34.20 | 2.2 |
| Blood | 17.4 | 1.5 | 3.08 | 0.73 |
| Muscle | 28.0 | 1.1 | 6.6 | 0.7 |
| Lung | 1.71 | 0.37 | 0.28 | 0.04 |
| Liver | 3.18 | 0.61 | 0.65 | 0.07 |
| Liver + GI | 9.6 | 1.4 | 2.1 | 0.2 |
| Kidney + Urine | 12.8 | 0.6 | 45.9 | 2.5 |
| | Counts/Gram ratio | | | |
| Bone/Blood | — | — | 13.78 | 4.37 |
| Bone/Muscle | — | — | 45.05 | 5.74 |
| Bone/Liver | — | — | 54.65 | 9.94 |

EXAMPLE 13

The preparation and characterisation of the [Tc(II)(NO)Cl$_4$]$^-$ anion

Tc-99

To an aqueous solution of ammonium pertechnetate (1 ml., 0.15 mM) was added concentrated hydrochloric acid (1 ml) and the mixture heated for 30 minutes in a pressure cooker. The product of the reaction is [TcCl$_6$]$^{2-}$ as the yellow ammonium salt. The resulting solution was cooled, diluted with water (1 ml), mixed with a solution of hydroxylamine in water (1 ml, 2.3 m), and heated for a further 30 minutes in a pressure cooker. The resulting green solution contains the species [Tc(NO)Cl$_4$]$^-$ which is formed quantitatively. The anion can be isolated as the tetra-butylammonium salt by addition of tetra-butylammonium chloride solution (75% aqueous solution) and quantitative extraction of the green compound into dichloromethane. Removal of the dichloromethane allows recrystallisation of [TcNOCl$_4$(CH$_3$OH)] (n-Bu)$_4$N from methanol and ether.

This complex readily undergoes ligand exchange with a variety of ligands. It is not necessary to recrystallise the product before use.

The analogous technetium nitrosyl tetra-bromide and -iodide can prepared substituting the corresponding acid and tetra-butylammonium halide.

Tc-99m

To 1 ml of generator eluant was added 1 ml of concentrated HCl. The mixture was heated in a pressure cooker for 30 minutes. The product of the reaction is ammonium hexachlorotechnetate. The resulting solution was cooled, diluted with water (1 ml), mixed with a solution of hydroxylamine hydrochloride (1 ml, 2.3M) and heated for a further 30 minutes. The resulting solution contains the species [Tc(NO)Cl$_4$]$^-$. The product can be utilised in two ways:

a) By the addition of 0.1 ml of 7.0% tetrabutylammonium chloride solution, extraction into dichloromethane, evaporation to dryness and redissolution in saline or other suitable solvent, such as aqueous alcohol, for further reaction. This method removes any excess hydroxylamine and chloride ions.

b) Reaction with ligand and then purification by separation of the ligand exchange product and starting material.

Results (Tc-99 and Tc-99m)

Paper Chromatography (Identical for Tc-99 and Tc-99m)

| Complex | Rf in butan-2-one | Rf in saline |
|---|---|---|
| $TcO_4^-$ | 0.92 | 0.73 |
| $TcCl_6^{2-}$ | 0.37 | 0.76 |
| $Tc(NO)Cl_4^-$ | 0.70 | 0.80 |
| $(Bu_4N)Tc(NO)Cl_4$ | 0.82 | 0.82 |

Electrophoresis $Tc(NO)Cl_4^-$ moves as an anion with a mobility of half that of $TcO_4^-$.

Infra-Red Spectrum (KBr disc) Adsorptions at 1805 cm$^{-1}$ for v(NO) and 326 cm$^{-1}$ for v(Tc-Cl).

Crystal Structure

The tetra-n-butylammonium tetrachloro(methanol) nitrosyltechnetium (II), $[(C_4H_9)_4N][Tc(NO)Cl_4(CH_3OH)]$ crystal is monoclinic, space group $P2_1/n$, a=11.350, b=11.450, c=22.154A, =91.5°, R=0.051.

The anion $[Tc(NO)Cl_4(CH_3OH)]^-$ has a distorted octahedral geometry with the four chlorine atoms lying in an equatorial plane with the Tc 0.15A above towards the nitrosyl. The nitrosyl group is bonded almost linearly to the technetium and the co-ordinated methanol trans to it was found to be hydrogen bonded to a methonal of solvation.

Figure 1:
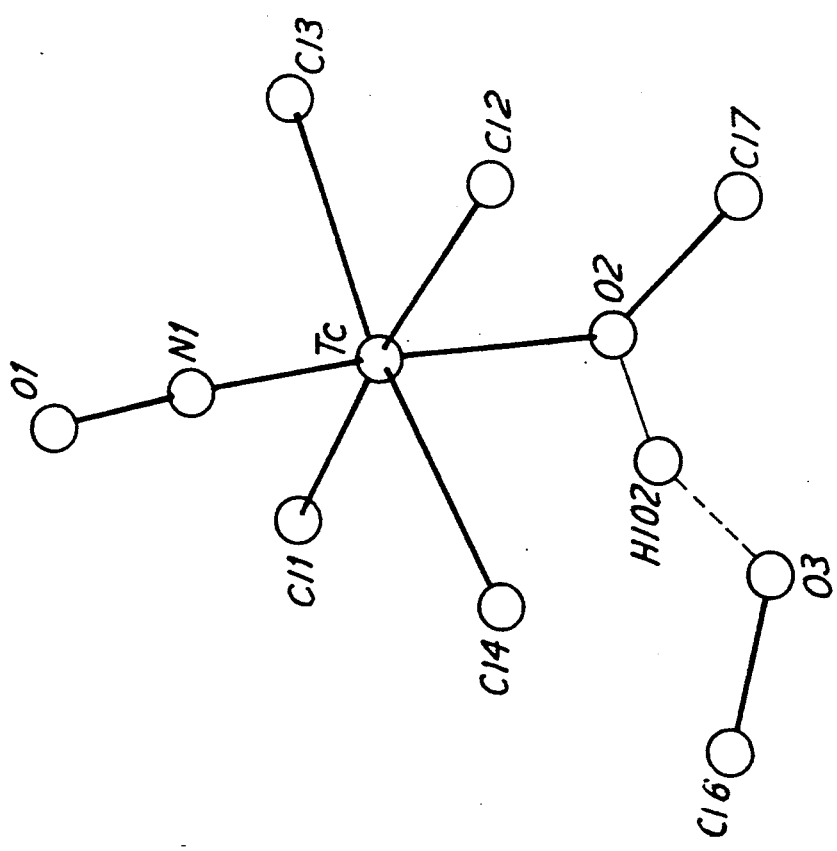
FIG. 1 shows the molecular structure of the anion [Tc(NO)Cl$_4$]$^-$, (Example 13).

FIG. 1 shows the molecular structure and atom numbering for the anion and solvated methanol with hydrogen bonding.

Table 14 gives animal biodistribution data in rats.

TABLE 14
ANIMAL BIODISTRIBUTION DATA IN RATS $[^{99m}TcNOCl_4]^-$

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 0.55 | 0.06 | 0.42 | 0.07 |
| Blood | 20.32 | 1.77 | 14.94 | 1.83 |
| Muscle | 30.35 | 7.96 | 30.41 | 9.06 |
| Lung | 2.09 | 1.15 | 1.71 | 0.25 |
| Liver | 5.31 | 0.93 | 4.59 | 0.49 |
| Liver + GI | 13.49 | 2.8 | 11.89 | 1.34 |
| Kidney + Urine | 6.26 | 0.98 | 14.61 | 9.72 |
| Brain | 0.09 | 0.06 | 0.05 | 0.01 |
| | Counts/Gram ratio | | | |
| Heart/Blood | 0.41 | 0.05 | 0.43 | 0.10 |
| Heart/Muscle | 2.14 | 0.55 | 1.66 | 0.63 |
| Heart/Liver | 1.37 | 0.26 | 0.98 | 0.27 |

EXAMPLE 14

The preparation and characterisation of the $[Tc^{II}(NO)(acac)Cl_3]^-$ anion (acac=pentan-2,4-dione ($CH_3COCH_2COCH_3$))

Tc-99

To an aqueous solution of ammonium pertechnetae (1 ml., 0.15 mM) was added concentrated hydrochloric acid (1 ml) and the mixture heated for 30 minutes. The product of the reaction is $[TcCl_6]^{2-}$ as the yellow ammonium salt. The resulting solution was cooled, diluted with water (1 ml), mixed with a solution of hydroxylamine in water (1 ml, 2.3M), and heated for a further 30 minutes. The resulting green solution contains the species $[Tc(NO)Cl_4]^-$. To this solution was added acetylacetone (0.5 ml, 5 mM) and the solution heated under pressure for a further 30 minutes. From the red solution produced the product was extracted into dichloromethane (10 ml) leaving the unreacted $[Tc(NO)Cl_4]^-$ in the aqueous phase. Evaporation of the dichloromethane layer gave a red oily residue which was redissolved in methanol:water (80:20) (5 ml). Addition of tetraphenylarsonium chloride (0.02 g in 1 ml of methanol) followed by evaporation of the solution to a low volume gave a red precipitate. Recrystallisation of this red solid from methanol/water gave kite shaped plates suitable for X-ray analysis.

Tc-99m

To 1 ml of generator eluant was added concentrated hydrochloric acid (1 ml) and the mixture heated under pressure for 30 minutes. The product of the reaction is ammonium hexachlorotechnetate. The resulting solution was cooled, diluted with water (1 ml), mixed with a solution of hydroxylamine hydrochloride (1 ml, 2.3M) and heated for a further 30 minutes. The resulting solution contains the species $[Tc(NO)Cl_4]^-$. To this solution was added acetylacetone (0.35 ml, 5 mM) and the solution heated under pressure for a further 30 minutes. The complex was adsorbed onto a millipore filter and eluted with 50:50 ethanol:water to give a pure complex free of unreacted starting materials.

Results

Paper Chromatography (Tc-99 and Tc-99m)

| Complex | Rf in butan-2-one | Rf in saline |
|---|---|---|
| $[Tc(NO)(acac)Cl_3]^-$ | 0.03 | 0.80 |

Electrophoresis (Tc-99 and Tc-99m)

The complex decomposed under electrophoretic conditions.

HPLC (Tc-99m)

Retention time 4.0 minutes.

Infra-Red Spectrum (Tc-99)

(KBr disc) Adsorptions at 1770 cm$^{-1}$ for v(NO) and 320 cm$^{-1}$ for v(Tc-Cl). Other adsorptions as expected for co-ordinated acetylacetone.

Analysis (Tc-99)

Calculated for $C_{29}H_{27}NO_3TcAs$ C 48.81 (48.50); H 3.79 (3.76); N 1.89 (1.95).

Fast Atom Bombardment (FAB)

The FAB$^-$ mass spectrum has a major ion at $m/z$=333 (calculated for $C_5H_7NO_3Tc$ $m/z$ 333) due to $[Tc(NO)(acac)Cl_3]^-$ with the expected isotope pattern due to the three chlorine atoms. Fragmentation occurs via the loss of 1 chlorine to $m/z$=298. The ions at $m/z$=269 and 262 correspond to $[M-Cl-NO+H]^-$ and $[M-2Cl+H]^-$ respectively. Then other lower mass ions at 23 and 204 are due to $[Tc(acac)]^-$ and $[TcCl_3]^-$.

FIG. 2 shows the molecular structure and atom numbering for the trichloro(pentan-2,4-dionato) nitrosyltechnetium(II) anion. One of the disordered arrangements is shown where N(3), O(3) and Cl(4) are the disordered atoms.

Table 15 gives biodistribution results in rats (mean of 2 animals).

TABLE 15

ANIMAL BIODISTRIBUTION DATA IN RATS
[$^{99}$Tc(NO)Cl$_3$(acac)]$^-$

|  | Time p.i. in vivo | | | |
|---|---|---|---|---|
|  | 2 min | | 60 min | |
|  | Mean | Std. Dev. | Mean | Std. Dev. |
| | % injected dose/organ | | | |
| Heart | 0.56 | — | 0.23 | — |
| Blood | 3.56 | — | 2.00 | — |
| Muscle | 27.9 | — | 14.37 | — |
| Lung | 0.73 | — | 0.53 | — |
| Liver | 3.12 | — | 8.27 | — |
| Liver + GI | 0.00 | — | 0.00 | — |
| Kidney + Urine | 1.61 | — | 13.55 | — |
| Brain | 0.10 | — | 0.05 | — |
| | Counts/Gram ratio | | | |
| Heart/Blood | 2.2 | — | 1.76 | — |
| Heart/Muscle | 2.19 | — | 1.84 | — |
| Heart/Liver | 2.30 | — | 0.39 | — |
| Heart/Lung | 1.12 | — | 0.74 | — |

EXAMPLE 15

The preparation and characterisation of the complexes [Tc(I)(NO)(phen)$_2$Cl]$^+$ and [Tc(II)(NO)(phen)Cl$_3$]

phen = 1,10-phenanthroline

[Tc(NO)(phen)$_2$Cl]$^+$ (Tc-99)

To an aqueous solution of ammonium pertechnetae (1 ml., 0.15 mM) was added concentrated hydrochloric acid (1 ml) and the mixture heated for 30 minutes. The product of the reaction is [TcCl$_6$]$^{2-}$ as the yellow ammonium salt. The resulting solution was cooled, diluted with water (1 ml), mixed with a solution of hydroxylamine in water (1 ml, 2.3M), and heated for a further 30 minutes. The resulting green solution contains the species [Tc(NO)Cl$_4$]$^-$. Addition of tetrabutylammonium chloride solution (75% in water) allowed extraction of the [Tc(NO)Cl$_4$]$^-$ dichloromethane (5 ml). The dichloromethane was evaporated off to leave a green solid which was redissolved in methanol (10 ml) and phen (54 mg, 3 mM) added. The mixture was stirred until a dark green colour resulted. Slow evaporation of the solvent led to the formation of dark green crystals.

[Tc(NO)(phen)$_2$Cl]$^+$ Tc-99m

To 1 ml of generator eluant was added 1 ml of concentrated HCl. The mixture was heated in a pressure cooker for 30 minutes. The product of the reaction is ammonium hexachlorotechnetate. The resulting solution was cooled, diluted with water (1 ml), mixed with a solution of hydroxylamine hydrochloride (1 ml, 2.3M) and heated for a further 30 minutes. The resulting solution contains the species [Tc(NO)Cl$_4$]$^-$. To this solution was added a solution of phen (1 ml, 80 mM in 50:50 ethanol:water). The solution was allowed to react at room temperature for 1.5 hours.

[Tc(NO)(phen)Cl$_3$] (Tc-99)

To an aqueous solution of ammonium pertechnetate (1 ml., 0.15 mM) was added concentrated hydrochloric acid (1 ml) and the mixture heated for 30 minutes in a pressure cooker. The product of the reaction is [TcCl$_6$]$^{2-}$ as the yellow ammonium salt. The resulting solution was cooled, diluted with water (1 ml), mixed with a solution of hydroxylamine in water (1 ml, 2.3M), and heated for a further 30 minutes in a pressure cooker. The resulting green solution contains the species [Tc(NO)Cl$_4$]$^-$. To 2 ml of this solution was added phen (33 mg, 0.18 mM) and ethanol (1 ml). The mixture was heated in a pressure cooker for 30 minutes. The reaction mixture was allowed to cool undisturbed while the product crystallised out as dark green needles.

Results

Paper Chromatography (Tc-99m)

| Complex | Rf in butan-2-one | Rf in saline |
|---|---|---|
| [Tc(NO)(phen)$_2$Cl]$^+$ | 0.85 | 0.89 |

Electrophoresis (Tc-99m)

The complex [Tc(NO)(phen)$_2$Cl]$^+$ moves a distance of 2.2 cm per hour (2.68 Vcm$^{-2}$) towards the cathode.

Infra-Red Spectrum (KBr disc) [Tc(NO)(phen)$_2$Cl]$^+$ has v(NO) at 1800 cm$^{-1}$ and v(Tc-Cl) at 340 cm$^{-1}$ [Tc(NO)(phen)Cl$_3$] has v(NO) at 1770 cm$^{-1}$ and v(Tc-Cl) at 330 cm$^{-1}$.

Analysis (Tc-99)

Calculated for C$_{12}$H$_8$N$_3$OCl$_3$Tc.HCl: C 31.3 (31.8); H 1.8 (2.0); N 9.7 (9.3)%.

FABMS (Tc-99)

The FAB$^+$ mass spectrum of [Tc(NO)(phen)$_2$Cl]$^{30}$ has a major ion at $m/z$=524 (calculated for C$_{24}$H$_{16}$N$_5$OClTc $m/z$=524) the FAB mass spectrum of [Tc(NO)(phen)Cl$_3$] has a major ion at $m/z$=414 (calculated for C$_{12}$H$_8$N$_3$OCl$_3$Tc $m/z$=414). Fragmentation occurs by the loss of each chlorine to $m/z$=379 [Tc(NO)(phen)Cl$_2$], $m/z$=344 [Tc(NO)(phen)Cl] and $m/z$=309 [Tc(NO)(phen)].

Biodistribution results are given in Table 16.

TABLE 16

ANIMAL BIODISTRIBUTION DATA
[$^{99}$Tc(NO)(1,10 phen)Cl$_3$]*

|  | Time p.i. in vivo | | | |
|---|---|---|---|---|
|  | 2 min | | 60 min | |
|  | Mean | Std. Dev. | Mean | Std. Dev. |
| | % injected dose/organ | | | |
| Heart | 0.40 | 0.13 | 0.29 | 0.03 |
| Blood | 3.98 | 1.37 | 3.49 | 0.67 |
| Muscle | 22.83 | 5.35 | 17.02 | 0.99 |
| Lung | 0.67 | 0.45 | 0.23 | 0.11 |
| Liver | 0.16 | 0.03 | 0.46 | 0.26 |
| Kidney + Urine | 1.97 | 1.17 | 16.05 | 1.21 |
| Brain | 0.08 | 0.03 | 0.04 | 0.00 |
| | Counts/Gram ratio | | | |
| Heart/Blood | 1.59 | 0.38 | 1.36 | 0.19 |
| Heart/Muscle | 1.99 | 0.47 | 4.68 | 4.53 |
| Heart/Liver | 35.14 | 17.06 | 10.63 | 5.60 |
| Heart/Lung | 1.55 | 1.16 | 2.57 | 1.11 |

EXAMPLE 16

The preparation and characterisation of the complex [Tc$^{II}$(NO)(bipy)Cl$_3$]° bipy = 2,2'-bipyridyl

Tc-99

To an aqueous solution of ammonium pertechnetae (1 ml., 0.15 mM) was added concentrated hydrochloric acid (1 ml) and the mixture heated for 30 minutes. The product of the reaction is [TcCl$_6$]$^{2-}$ as the yellow ammonium salt. The resulting solution was cooled, diluted with water (1 ml), mixed with a solution of hydroxylamine in water (1 ml, 2.3M), and heated for a further 30 minutes. The resulting green solution contains the species [Tc(NO)Cl$_4$]$^-$. To 2 ml of this solution was added bipy (32 mg, 0.2 mM) and ethanol (1 ml) and the mixture heated in the pressure cooker for 30 minutes. The reaction solution was allowed to cool undisturbed while the product crystallised out as green needles.

Tc-99m

To 1 ml of generator eluant was added 1 ml of concentrated HCl. The mixture was heated in a pressure cooker for 30 minutes. The product of the reaction is ammonium hexachlorotechnetate. The resulting solution was cooled, diluted with water (1 ml), mixed with a solution of hydroxylamine hydrochloride (1 ml, 2.3M) and heated for a further 30 minutes. The resulting solution contains the species [Tc(NO)Cl$_4$]$^-$. To this solution was added bipy (1.5 ml, 0.1M in 50:50 ethanol:water) and the reaction was allowed to proceed at room temperature for 2 hours.

Results

Paper Chromatography (Tc-99m)

| Complex | Rf in butan-2-one | Rf in saline |
|---|---|---|
| [Tc(NO)(bipy)Cl$_3$] | 0.85 | 0.89 |

Electrophoresis (Tc-99m)

The complex does not move under electrophoresis conditions because it is neutral.

Infra-Red Spectrum (Tc-99)

(KBr disc) Adsorptions at 1780 cm$^{-1}$ for v(NO) and 326 cm$^{-1}$ for v(Tc-Cl).

Crystal Structure (Tc-99)

The bipyridyltrichloronitrosyltechnetium (II) [Tc(NO)(C$_{10}$H$_8$N$_2$)Cl$_3$] crystal is monoclinic, space group P2$_1$/c, a=8.18, b=6.90, c=13.124A, β=112.16

This complex is neutral.

Table 17 gives biodistribution results in rats (average of 2 animals).

TABLE 17

ANIMAL BIODISTRIBUTION DATA IN RATS [$^{99}$Tc(NO)Cl$_3$(Bipy)]

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 0.32 | — | 0.30 | 0.05 |
| Blood | 7.17 | — | 2.02 | 0.36 |

TABLE 17-continued

ANIMAL BIODISTRIBUTION DATA IN RATS [$^{99}$Tc(NO)Cl$_3$(Bipy)]

| | Time p.i. in vivo | | | |
|---|---|---|---|---|
| | 2 min | | 60 min | |
| | Mean | Std. Dev. | Mean | Std. Dev. |
| Muscle | 24.17 | — | 18.95 | 3.76 |
| Lung | 0.45 | — | 0.10 | 0.03 |
| Liver | 3.43 | — | 3.35 | 0.53 |
| Liver + GI | 0.00 | — | 0.00 | 0.00 |
| Kidney + Urine | 11.30 | — | 22.96 | 6.88 |
| Brain | 0.06 | — | 0.04 | 0.01 |
| | Counts/Gram ratio | | | |
| Heart/Blood | 0.99 | — | 2.12 | 0.92 |
| Heart/Muscle | 1.69 | — | 2.02 | 0.36 |
| Heart/Liver | 1.31 | — | 1.09 | 0.18 |
| Heart/Lung | 1.30 | — | 4.13 | 0.87 |

EXAMPLE 17

The preparation and characterisation of the cation [Tc$^I$(NO)(t-BuNC)$_4$Cl]$^+$ (t-BuNC = tertiary-butylisonitrile (CH$_3$)$_3$CNC)

(Tc-99)

To an aqueous solution of ammonium pertechnetae (1 ml., 0.15 mM) was added concentrated hydrochloric acid (1 ml) and the mixture heated for 30 minutes. The product of the reaction is [TcCl$_6$]$^{2-}$ as the yellow ammonium salt. The resulting solution was cooled, diluted with water (1 ml), mixed with a solution of hydroxylamine in water (1 ml, 2.3M), and heated for a further 30 minutes. The resulting green solution contains the species [Tc(NO)Cl$_4$]$^-$. Addition of tetrabutylammonium chloride solution (75% in water) allowed extraction of the [Tc(NO)Cl$_4$]$^-$ into dichloromethane (5 ml). The dichloromethane was evaporated off to leave a green solid which was redissolved in ethanol (20 ml) and t-BuNC (0.055 ml, 0.9 mM) added. The mixture was refluxed under nitrogen for 3 hours undergoing a colour change from bright green through dark green to pale yellow. The reaction mixture was cooled in ice and sodium hexafluorophosphate (100 mg in 1 ml) added. The white precipitate of tetrabutylammoniumhexafluorophosphate was removed by filtration. The solvent was evaporated down to 10 ml and the product crystallised as fine pale yellow needles on cooling.

Results

Electrophoresis

The complex moves 2.0 cm (8.75 Vcm$^{-1}$) in 1 hour toward the cathode.

Infra-Red Spectrum (KBr disc) Adsorptions at 1765 cm$^{-1}$ for v(NO), 2195 cm$^{-1}$ for v(CN).

$^1$H NMR

Confirms four equivalent (t-BuNC) groups.

(+) FABMS

The FAB mass spectrum has a major ion at $m/z$=496 (calculated for (C$_{20}$H$_{36}$N$_5$ClOTc $m/z$=496). Fragmentation occurs via loss of a t-BuNC group to [Tc(NO)(t-BuNC)$_3$Cl]$^+$ $m/z$=413.

Table 18 gives biodistribution results.

TABLE 18

ANIMAL BIODISTRIBUTION DATA IN RATS
[$^{99}$Tc(NO)Cl(t-BuCN)$_4$]$^+$

| | Time p.i. in vivo | | | |
|---|---|---|---|---|
| | 2 min | | 60 min | |
| | Mean | Std. Dev. | Mean | Std. Dev. |
| | % injected dose/organ | | | |
| Heart | 1.09 | 0.28 | 1.37 | 0.28 |
| Blood | 0.40 | 0.66 | — | — |
| Muscle | 21.45 | 3.44 | 18.30 | 3.07 |
| Lung | 0.64 | 0.40 | 0.12 | 0.09 |
| Liver | 5.82 | 1.48 | 5.89 | 0.36 |
| Kidney + Urine | 6.86 | 6.58 | 8.15 | 5.95 |
| Brain | 0.04 | 0.01 | 0.04 | 0.02 |
| | Counts/Gram ratio | | | |
| Heart/Blood | 6.19 | 1.73 | 8.98 | 2.95 |
| Heart/Liver | 2.58 | 0.20 | 2.97 | 0.34 |
| Heart/Lung | 3.34 | 2.35 | 26.02 | 20.6 |

EXAMPLE 18

The preparation and characterisation of the cation $[Tc^I(NO)(RNH_2)_4(H_2O)]^{2+}$ R=H, alkyl Tc-99m To 1 ml of generator eluant was added 1 ml of concentrated HCl. The mixture was heated in a pressure cooker for 30 minutes. The product of the reaction is ammonium hexachlorotechnetate. The resulting solution was cooled, diluted with water (1 ml), mixed with a solution of hydroxylamine hydrochloride (1 ml, 2.3M) and heated for a further 30 minutes. The resulting solution contains the species [Tc(NO)Cl$_4$]$^-$. This solution is then neutralised with C$_2$H$_5$NH$_2$ to pH 7.5. Heat for 15 minutes on a waterbath.

Results

Paper Chromatography (Tc-99m)

| Rf in butan-2-one | Rf in saline |
|---|---|
| 0.05 | 0.83 |

This complex is cationic.

Analogous Complexes (Tc-99m)

Complexes of the type [Tc(NO)L$_2$(H$_2$O)]$^{2+}$ where L is a derivative of ethylenediamine (en) may be prepared.

To 1 ml of generator eluant was added 1 ml of concentrated HCl. The mixture was heated in a pressure cooker for 30 minutes. The product of the reaction is ammonium hexachlorotechnetate. The resulting solution was cooled, diluted with water (1 ml), mixed with a solution of hydroxylamine hydrochloride (1 ml, 2.3M) and heated for a further 30 minutes. The resulting solution contains the species [Tc(NO)Cl$_4$]$^-$. This solution is then neutralised with diamine pH 7.5. Heat for 15 minutes on a waterbath.

Results

Paper Chromatography (Tc-99m)

| Rf in butan-2-one | Rf in saline |
|---|---|
| 0.05 | 0.89 |

Electrophoresis

This complex moves as a cationic.

| Distance moved in 1 hour (cm) | Volts/cm |
|---|---|
| 0.60 | 1.82 |

EXAMPLE 19

The chunky crystals of the complex [Tc(NO)(Ph$_2$PCH$_2$CH$_2$PPh$_2$)$_2$Cl][Cl] proved suitable for X-ray structure analysis. The objective was to confirm the nature of the complex and to determine the overall molecular configuration, to correlate with data in Tables 8 and 9 above.

Figure 3:
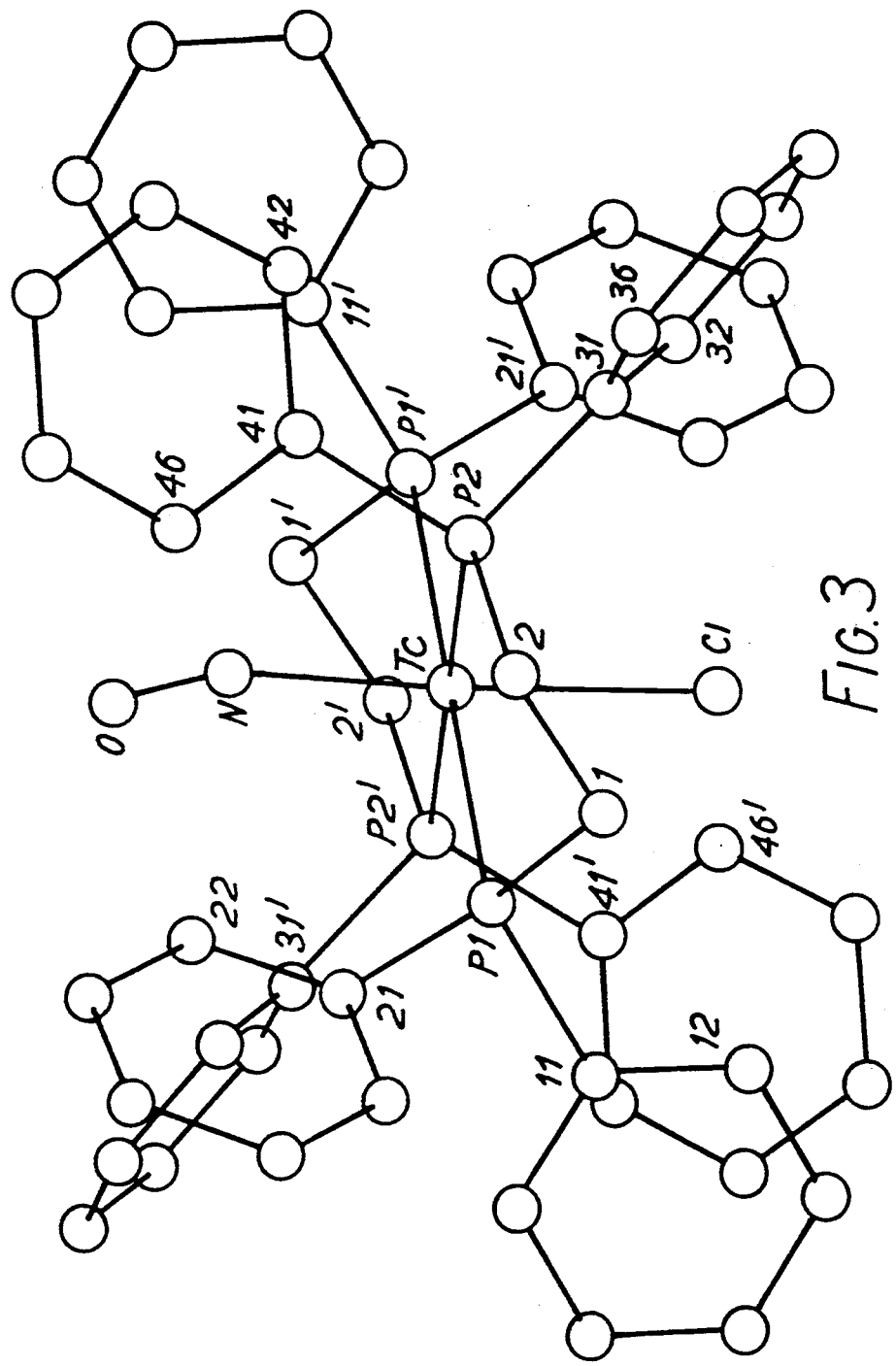
FIG. 3 shows the molecular structure of [Tc(NO)(dppe)$_2$Cl]$^+$, (Examples 5 and 19).

The single crystal X-ray diffraction study confirms the formulation of the complex as [Tc(NO)(Ph$_2$PCH$_2$CH$_2$PPh$_2$)$_2$Cl][Cl], and indicates that there is one molecule of water co-crystallising per molecule of complex. The complex cation has the slightly distorted octahedral co-ordination shown in FIG. 3. The equatorial sites are occupied by the phosphorus donor atoms of the two bidentate bis-(diphenylphosphino)ethane (dppe) ligands. A nitrosyl and a chloro ligand occupy the axial sites.

Evidence presented in Table 8 above confirms that the Tc-99m complex has the same physical properties and therefore the same structure as the Tc-99 complex.

Further evidence for the presence of the NO-moiety is provided by $^{15}$N labelling of the $^{99}$Tc complex [$^{99}$Tc($^{15}$NO)(dppe)$_2$Cl]$^+$. This complex was synthesised from $^{15}$NH$_2$OH.HCl. The $^{99}$Tc product species exhibits a characteristic isotope shift (reduction in stretching frequency) of the NO-group, associated with the presence of the stable $^{15}$N atom within the NO-moiety Table 9.

ANIMAL BIODISTRIBUTION RESULTS

In all of the $^{99m}$Tc-nitrosyl complexes examined, the presence of the Tc-(NO) moiety significantly changes the animal biodistributions of the product radiopharmaceutical e.g. with respect to:
a) diphosphine analogues such as [Tc$^{III}$Cl$_2$(dmpe)$_2$]$^+$ or [Tc$^I$(dmpe)$_3$]$^+$.
b) d,1-HMPAO, Ceretec [Tc(0) (HMPAO)].

In the case of the former, two key features are heart uptake and retention and the clearance from blood and liver, not normally associated with phosphine complexes. In the latter, the key feature is formation of cationic hydrophilic derivatives of d,1-HMPAO which no longer show the significant brain uptake associated with neutral lipophilic materials.

STABILITY STUDIES

Stability studies on the $^{99m}$Tc and $^{99m}$Tc-nitrosyl intermediates and product complexes indicate that they are highly stable in aqueous solution, the $^{99}$Tc complexes being indefinitely stable in air under ambient conditions in the solid state.

CHROMATOGRAPHY AND HPLC RESULTS

Table 8 shows good correlation of chromatographic and HPLC data between the examples of the $^{99m}Tc$ radiopharmacetucals and their $^{99}Tc$ analogues.

INFRA RED SPECTROSCOPY RESULTS a) The form of the "intermediate" nitrosyl complexes are not presently well understood. Formulation as low oxidation state complexes of $Tc^I$ or $Tc^{II}$ intermediates is based on i-r $\nu(NO)$ comparisons with 99-technetium nitrosyl compounds observed in the literature, none of which are found in oxidation states $>Tc^{3+}$. The true oxidation state of these intermediates will be explored and verified as soon as possible.

| | |
|---|---|
| Tc-(NO) sulphate intermediate | $\nu(NO) = 1830$ cm$^{-1}$ |
| Tc-(NO) chloride intermediate | $\nu(NO) = 1780$ cm$^{-1}$ |
| $[Tc^{II}(NO)(NH_3)_4(H_2O)]^{3+}$ (1) | $\nu(NO) = 1815$ cm$^{-1}$ |
| $[Tc^{II}(NO)(Cl)_5]^{2-}$ (1) | $\nu(NO) = 1803$ cm$^{-1}$ |
| $[Tc^{II}(NO)(NCS)_5]^{2-}$ (2) | $\nu(NO) = 1785$ cm$^{-1}$ |
| $[Tc^{II}(NO)Cl_3(PEt_2Ph)_2]$ (3) | $\nu(NO) = 1775$ cm$^{-1}$ |
| $[Tc^{II}(NO)Cl_3(PMe_2Ph)_2]$ (4) | $\nu(NO) = 1795$ cm$^{-1}$ and 1770 cm$^{-1}$ |
| $[Tc^I(NO)(NH_3)_4(H_2O)]^{2+}$ | $\nu(NO) = 1690$ cm$^{-1}$ |
| $[Tc^I(NO)(NCS)_5]^{3-}$ (2) | $\nu(NO) = 1690$ cm$^{-1}$ |
| $[Tc^I(NO)(NH_3)(1,10\text{-phen})_2]^{2+}$ | $\nu(NO) = 1712$ cm$^{-1}$ |
| $[Tc^I(NO) (=N\text{-Bu}^t)_5]^{2+}$ (5) | $\nu(NO) = 1865$ cm$^{-1}$ |
| $[Tc^I(NO) Br_2 (C=N\text{-Bu}^t)_3]$ (5) | $\nu(NO) = 1775$ cm$^{-1}$ | b) There is little doubt that the phosphine complexes characterised in Table 9 are $Tc^I$ diamagnetic complexes, which are presently undergoing nmr spectroscopic investigation.

CONCLUSION

The simple one-step synthesis of Technetium-Nitrosyl core systems, and their liability towards chemical substitution reactions with various ligands create a wide scope for the development of novel $^{99m}Tc$ radiopharmaceuticals, containing the Tc-(NO) moiety. These processes allow easy access to new low oxidation state Tc radiopharmaceuticals.

EXPERIMENTAL

Reagents

Hydroxylamine salts $NH_2OH.HCl$, $(NH_2OH)_2.H_2SO_4$ were purchased from Aldrich Chemical Co. Ltd.; solvents were of AnalaR grade; bis(dimethylphosphino)ethane (DMPE), bis(diethylphosphino)ethane and bis(diphenylphosphine)-ethane were purchased from Strem Chemicals Inc., and used as received.

Chromatography

Samples were supplied by needle approximately 2.5 cm from the bottom of two Gelman ITLC/SG strips (2.5 cm×20 cm) and one Whatman No. 1 strip (2.5 cm×20 cm) and then immediately placed in prepared ascending chromatography development tanks containing fresh solvent (1 cm), (a) Saline, (b) Methyl ethyl ketone, and (c) 50:50 acetonitrile/water, respectively. After 15 cm elution the strips are removed, solvent fronts marked, dried and the distribution of activity determined using suitable equipment.

Electrophoresis

A 0.1 g Agarose/10 cm$^3$ 50 mM Phosphate buffer pH 7.4 gel was run at an applied potential of 300 VV for approximately 35 mins, using bromophenol blue indicator (this indicator moves towards the cathode). The resulting distribution of activity was determined using suitable equipment.

HPLC

A solvent, gradient HPLC system was used in conjunction with
(a) 20 mM phosphate buffer pH 7.4
(b) Tetrahydrofuran (Thf).

Samples are applied initially at 100% (a), the gradient changing to 100% (b) in approximately 17 minutes. Flow rate=2 ml/min Hamilton PRP column (15 cm×4.0 mm) ambient temperature. Identical HPLC systems were used for $^{99m}Tc$ and $^{99}Tc$ determinations, $^{99m}Tc$ detected by emission, $^{99}Tc$ detected via liquid scintillation method.

ANIMAL BIODISTRIBUTION

In vivo studies

In vivo biodistribution 0.1 ml $Tc^{99m}$ prep was injected i.v. into a lateral tail vein of 6 anaesthetised rats.

At 2 minutes and 60 minutes post injection, 3 rats were sacrificed by decapitation, bled from the neck and dissected. The following organs were removed at dissection: kidney, bladder(+urine), lung, liver, spleen, stomach, small intestine, large intestine, brain (weighed), heart (weighed), thyroid, and samples of blood (weighed) and muscle (weighed, the residual carcass and the tail (injection site). Subsequently samples were counted in an automatic twin crystal gamma counter.

Percentage biodistribution of injected material was calculated (after correction for background) for all organs using the formula:

$$\frac{\% \text{ injected}}{\text{dose}} = \frac{\text{counts/organ}}{\text{total count in animal} - \text{count in tail}} \times 100$$

Since only samples of muscle and blood were taken, the percentage in these tissues was calculated assuming blood and muscle to represent 5.8 and 43% of total animal weight respectively using the formula:

$$\frac{\% \text{ injected}}{\text{dose in tissue}} = \frac{\text{Counts/gram tissue} \times CF \times \text{Bodyweight} \times 100}{\text{Total counts in animal} - \text{total counts in tail}}$$

where CF=
0.058 for blood
0.43 for blood.

REFERENCES

1) ARMSTRONG R. A., TAUBE H *Inorg. Chem.* (1976) 15 (8) p1904
2) ORVIG C., DAVISON A., JONES A. G. *J. Lab. Compounds and Radiopharmaceuticals* (1981) 18 p148.
3) FERGUSSON J. E., HEVELDT P. F. *J. Inorg. Nuc. Chem.* (1976) 38 p2231
4) KIRMSE R., LORENZ B., SCHMIDT K. *Polyhedron* (1983) 2 (9) p935

5) LINDER K. E., DAVISON A., DEWAN J. C., COSTELLO C. E., MALEKNIA S. *Inorg. Chem.* (1986) 25 p2085

6) SEIFERT S., SAYHRE R., MUNZE R., *Nuclearmed. Symp.*, Berlin (1984), p.82.

We claim:

1. A complex, useful as a diagnostic radiopharmaceutical, comprising the $^{99m}$Tc-NO nitrosyl moiety and up to four organic ligands which confer biological target-seeking properties on the complex.

2. The complex as claimed in claim 1 which is monocationic.

3. The complex as claimed in claim 2, the cation having the formula [$^{99m}$Tc(NO)L$_2$X]$^+$ where X is halide or pseudohalide and L is a bidentate ligand for technetium.

4. The complex as claimed in claim 3, wherein the ligand L is selected from phosphines and arsines of the general formula $$R_2Y(CZ_2)_nYR_2,$$

where

Y is P or As;

R is H or aryl or substituted or unsubstituted alkyl;

n is 1, 2, 3 or 4; and (CZ$_2$) is a substituted or unsubstituted methylene group.

5. The complex as claimed in claim 4, wherein

R is H, C1–C4 alkyl or phenyl; and (CZ$_2$)$_n$ is C$_2$H$_4$, C$_3$H$_6$ or 1,5-phenylene.

6. The complex as claimed in claim 3, where the ligand L is selected from phenanthroline and diamines.

7. The complex as claimed in claim 2, the cation having the formula [$^{99m}$Tc(NO)L′$_4$X]$^+$ where X is a halide or pseudohalide and L′ is a monodentate ligand for technetium selected from mono amines and isonitriles.

8. The complex as claimed in claim 1 which is monoanionic.

9. The complex as claimed in claim 8, including an anion having the formula [$^{99m}$Tc(NO)(acac)X$_3$]$^-$ where X is halide or pseudohalide and acac is pentane-2,4-dione.

10. The complex as claimed in claim 1 which is electrically neutral.

11. The complex as claimed in claim 10 having the formula [$^{99m}$Tc(NO)(bipyridyl)X$_3$]° where X is halide or pseudohalide.

* * * * *